(12) United States Patent
Matsumoto et al.

(10) Patent No.: US 10,527,572 B2
(45) Date of Patent: Jan. 7, 2020

(54) GAS SENSOR

(71) Applicant: Nissha Co., Ltd., Kyoto (JP)

(72) Inventors: Takashi Matsumoto, Kyoto (JP);
Mitsuharu Kira, Kyoto (JP); Hiroki Yamamoto, Kyoto (JP); Yuri Kuwahara, Kyoto (JP)

(73) Assignee: Nissha Co., Ltd., Kyoto (JP)

( * ) Notice: Subject to any disclaimer, the term of this patent is extended or adjusted under 35 U.S.C. 154(b) by 0 days.

(21) Appl. No.: 16/280,033

(22) Filed: Feb. 20, 2019

(65) Prior Publication Data

US 2019/0178829 A1 Jun. 13, 2019

Related U.S. Application Data

(63) Continuation of application No. PCT/JP2017/029947, filed on Aug. 22, 2017.

(30) Foreign Application Priority Data

Aug. 25, 2016 (JP) .................. 2016-164426

(51) Int. Cl.
*G01N 27/16* (2006.01)
*G01N 33/00* (2006.01)

(52) U.S. Cl.
CPC .......... *G01N 27/16* (2013.01); *G01N 33/005* (2013.01); *G01N 33/006* (2013.01)

(58) Field of Classification Search
CPC ..... G01N 27/16; G01N 33/005; G01N 33/006
USPC ...................................... 73/23.31
See application file for complete search history.

(56) References Cited

U.S. PATENT DOCUMENTS

| 2006/0219552 A1 | 10/2006 | Sasaki et al. |
| 2008/0092628 A1 | 4/2008 | Oishi et al. |
| 2011/0174052 A1 | 7/2011 | Kuebel |

FOREIGN PATENT DOCUMENTS

| JP | 2006-284498 A | 10/2006 |
| JP | 2007-040757 A | 2/2007 |
| JP | 2008-107137 A | 5/2008 |
| JP | 5927647 B2 | 6/2016 |

OTHER PUBLICATIONS

Decision to Grant a Patent received for Japanese Patent Application No. 2016-164426, dated Jul. 3, 2018, 6 pages including English Translation.

(Continued)

*Primary Examiner* — Daniel S Larkin
(74) *Attorney, Agent, or Firm* — Xsensus LLP

(57) ABSTRACT

A gas sensor, disposed projecting from a wiring member serving as a mounting target and including a first wire and a second wire, the gas sensor detecting a gas that produces water in a case that the gas is combusted by being supplied with a voltage from the first wire and the second wire and measuring a resistance value using the first wire and the second wire, the gas sensor including a resistor holding a catalyst that facilitates combustion of the gas, a first electrode terminal connected between one end of the resistor and the first wire, and a second electrode terminal connected between another end of the resistor and the second wire, and the first electrode terminal and the second electrode terminal are fixed to each other and form a water vapor diffusion cavity.

8 Claims, 17 Drawing Sheets

(56) References Cited

OTHER PUBLICATIONS

Notification of Reasons for Refusal received for Japanese Patent Application No. 2016-164426, dated Mar. 5, 2018, 6 pages including English Translation.
International Search Report dated Oct. 10, 2017 for PCT/JP2017/029947 filed on Aug. 22, 2017, 7 pages including English Translation.

GAS SENSOR

CROSS-REFERENCE TO RELATED APPLICATIONS

The present application is based on PCT filing PCT/JP2017/029947, filed Aug. 22, 2017, which claims priority to JP 2016-164426, filed Aug. 25, 2016, the entire contents of which are incorporated herein by reference

TECHNICAL FIELD

The present invention relates to a gas sensor that detects a gas which produces water when being combusted using a catalyst.

BACKGROUND ART

In recent years, hydrogen fuel cells are being put into practical use, giving rise to demand for gas sensors that detect hydrogen. Hydrogen is detected by a catalytic combustion gas sensor. This sensor uses a resistor holding a catalyst containing platinum, palladium, or rhodium, for example, which causes hydrogen to combust, on a metal wire formed from a metal such as platinum or palladium or an alloy thereof. The catalytic combustion gas sensor detects hydrogen using changes in the resistance value of the resistor, which occur when the hydrogen burns and the temperature rises.

Such gas sensors are sometimes used even in subzero environments. When a gas sensor is used in a subzero environment, water produced when hydrogen and oxygen combust freezes and forms frost around the gas sensor. In a case where the frost reaches the resistor, the frost will inhibit the diffusion of hydrogen and worsen the hydrogen detection accuracy. Accordingly, the gas detector disclosed in Patent Document 1 (JP 5927647 B) is configured such that a support part supporting a noble metal wire penetrates a circuit board, and a heating unit that heats the support part is provided on the side of the circuit board opposite from the side on which a housing containing a gas detection sensor is located.

CITATION LIST

Patent Literature

Patent Document 1: JP 5927647 B

SUMMARY OF INVENTION

Technical Problem

However, in a case that the gas detector includes the heating unit and the heat generated by the heating unit prevents the frost from being formed, the amount of power consumed greatly increases. For example, when a catalytic combustion gas sensor is installed in an automobile including a fuel cell, it is necessary to suppress the amount of power consumed by the catalytic combustion gas sensor to the greatest extent possible to avoid depleting the automobile's battery.

An object of the present invention is to provide a gas sensor having a small size and that can suppress gas detection problems caused by frost using only a small amount of power.

Solution to Problem

Some aspects are described below as the means to solve the problems. These aspects can be combined optionally, as needed.

A gas sensor according to one aspect of the present invention is a gas sensor, disposed projecting from a wiring member serving as a mounting target and including a first wire and a second wire, the gas sensor being configured to detect a gas that produces water in a case that the gas is combusted by being supplied with a voltage from the first wire and the second wire and measuring a resistance value using the first wire and the second wire. The gas sensor includes: a resistor holding a catalyst that facilitates combustion of the gas; a first electrode terminal connected between one end of the resistor and the first wire; and a second electrode terminal connected between another end of the resistor and the second wire. The first electrode terminal includes at least one first connection part connected to the first wire, and a first arm part extending from the at least one first connection part to the one end of the resistor. The second electrode terminal includes at least one second connection part connected to the second wire, and a second arm part extending from the at least one second connection part to the other end of the resistor. The first electrode terminal and the second electrode terminal are fixed to each other and form a water vapor diffusion cavity extending from the resistor to the wiring member or the vicinity of the wiring member, with at least part of the first arm part and at least part of the second arm part coated with insulation.

According to the gas sensor configured in this manner, the water vapor diffusion cavity, which extends from the resistor to the wiring member serving as a mounting target or the vicinity thereof, is formed between the resistor and the wiring member. Accordingly, water vapor produced when gas is combusted reaches the wiring member or the vicinity thereof through the water vapor diffusion cavity, and thus frost starts forming primarily on the wiring member or in the vicinity thereof. As a result, the combustion time necessary for frost to form can be increased, without consuming heating energy for melting the frost, while effectively using the entire lengths of the first arm part and the second arm part. This makes it possible to maintain a state where gas can be detected without being affected by frost for a long period of time.

In the above-described gas sensor, the first electrode terminal and the second electrode terminal may be bridged at substantially the same position as the resistor or a position further from the wiring member than a position of the resistor and fixed to each other. According to this configuration, the part bridging the first electrode terminal and the second electrode terminal is not present between the resistor and the wiring member. As a result, it is difficult for water vapor produced at the resistor to reach the bridged part. It is thus difficult for frost to start forming from the bridged parts, increasing the distance over which the frost propagates.

In the above-described gas sensor, the first arm part and the second arm part may be configured such that horizontal direction lengths of the first arm part and the second arm part expressed by X coordinates and Y coordinates in a plane perpendicular to a Z axis are substantially the same as vertical direction lengths of the first arm part and the second arm part expressed by Z coordinates and extending in a vertical direction from the wiring member. According to this configuration, the vertical direction size from the wiring member and horizontal direction size are suppressed, while at the same time making the combustion time over which detection can be carried out twice as long, or more, than in a case where the first arm part and the second arm part are erected straight in the vertical direction.

In the above-described gas sensor, both the first arm part and the second arm part may be bent into L shapes. By bending these parts into L shapes, using a simple structure, the distance along the first arm part and the second arm part over which frost propagates from the wiring member to the resistor can be increased while at the same time suppressing the vertical direction heights of the first electrode terminal and the second electrode terminal.

In the above-described gas sensor, the at least one first connection part includes first connection parts and the at least one second connection part includes second connection parts, the first arm part may branch and extend in two directions from the one end of the resistor, and include two first connection parts of the first connection parts connected to the first wire; and the second arm part may branch and extend in two directions from the other end of the resistor, and include two second connection parts of the second connection parts connected to the second wire. According to this configuration, the branching first arm part and the branching second arm part provide a total of four arms supporting the gas sensor, which improves the stability and strength with which the gas sensor is installed on the wiring member.

In the above-described gas sensor, the first arm part and the second arm part may be separated from each other and insulation-coated with a resin, from the vicinity of the at least one first connection part and the at least one second connection part to the vicinity of a position located at substantially the same height as the resistor. According to this configuration, the parts of the surfaces of the first electrode terminal and the second electrode terminal that are coated with resin, which makes it difficult for frost to propagate, can be lengthened. This makes it possible to improve the effect of suppressing problems caused by frost.

In the above-described gas sensor, the first arm part may include a first separation part that extends in a horizontal direction or an oblique direction from the one end of the resistor and allows the first arm part to be separated from the resistor in the horizontal direction, the first separation part being coated with a resin; and the second arm part may include a second separation part that extends in a horizontal direction or an oblique direction from the other end of the resistor and allows the second arm part to be separated from the resistor in the horizontal direction, the second separation part being coated with a resin. Coating the first separation part and the second separation part with resin in this manner makes it more difficult for frost to form than in a case where the first electrode terminal and the second electrode terminal are exposed, and thus situations where frost reaches the resistor can be suppressed.

The above-described gas sensor may be configured to further include a cap having a frame shape and configured to cover the resistor. Providing this cap makes it possible to protect the resistor when handling the gas sensor, while at the same time ensuring that the cap is not an obstruction when conducting the gas to be detected to the vicinity of the resistor. Accordingly, situations where defective devices are produced can be suppressed.

Advantageous Effects of Invention

According to the gas sensor of the present invention, it is easy to make the sensor more compact, and gas detection problems caused by frost can be suppressed using only a small amount of power.

DESCRIPTION OF EMBODIMENTS

First Embodiment

A gas sensor configured to detect hydrogen that produces water when combusted will be described hereinafter as an example of a gas sensor according to a first embodiment of the present invention. However, the detection target of the gas sensor according to the present invention is not limited to hydrogen. Methane, propane, and butane can also be given as examples of detection targets that produce water when combusted.

Before describing the gas sensor, a gas detection device using the gas sensor will be described briefly.

(1) Gas Detection Device Using Gas Sensor

Figure 1:
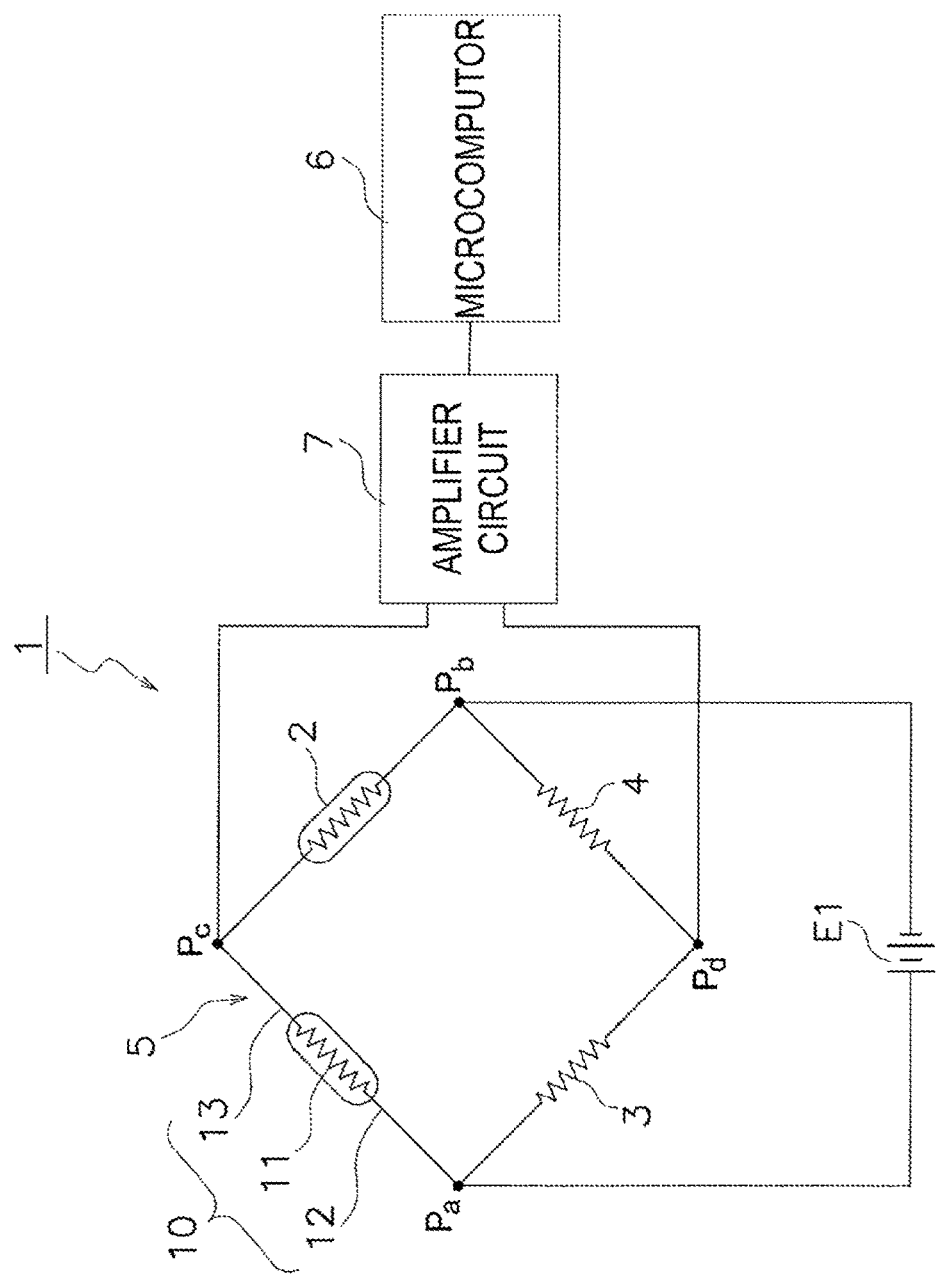
FIG. 1 is a circuit diagram illustrating an example of a gas detection device included in a gas sensor according to a first embodiment.

FIG. 1 schematically illustrates an example of a measurement circuit of a gas detection device 1 that uses a gas sensor 10. The measurement circuit of the gas detection device 1 includes a bridge circuit 5 constituted by the gas sensor 10, a compensation element 2, a first fixed resistor 3, and a second fixed resistor 4. A first electrode terminal 12, which is one terminal of the gas sensor 10, is connected to a connection point Pa, and a second electrode terminal 13, which is the other terminal of the gas sensor 10, is connected to a connection point Pc.

One terminal of the compensation element 2 is connected to the connection point Pc, and the other terminal of the compensation element 2 is connected to a connection point Pb.

Additionally, one terminal of the first fixed resistor 3 is connected to the connection point Pa, and the other terminal of the first fixed resistor 3 is connected to a connection point Pd. One terminal of the second fixed resistor 4 is connected to the connection point Pd, and the other terminal of the second fixed resistor 4 is connected to the connection point Pb.

The connection points Pd and Pc are output terminals of the bridge circuit 5, and a microcomputer 6 is connected to the connection point Pd and the connection point Pc with an amplifier circuit 7 therebetween. The microcomputer 6 has an AD conversion function, for example, and is configured to be capable of obtaining a potential difference arising between the connection point Pc and the connection point Pd as digital data.

The compensation element 2 is used to compensate for variations in the electrical resistance value of a resistor 11. Preferably, the compensation element 2 has operating characteristics that are the same as or similar to those of the gas sensor 10, but does not exhibit catalytic activity that causes hydrogen to combust. This compensation element 2 can be formed using, for example, the first electrode terminal 12 and the second electrode terminal 13 of the gas sensor 10, along with a platinum wire connected between those terminals. With this compensation element 2, for example, a catalyst is not held in a region corresponding to a catalyst holding region of the gas sensor 10, and a material which does not exhibit catalytic activity that causes hydrogen to combust is formed instead of the catalyst.

For example, when the gas detection device 1 is installed in an automobile, the configuration is such that a power supply E1 turns on at the same time as the automobile system starts, and the power supply E1 of the gas detection device 1 does not turn off until the automobile system is stopped. While the power supply E1 of the gas detection device 1 is on, the microcomputer 6 calculates a gas concentration from the output of the gas detection device 1 and outputs the result of the calculation. The power consumed by the gas sensor 10 at this time is set to a range, for example, from 10 mW to 100 mW.

(2) Gas Sensor Configuration

Figure 2:
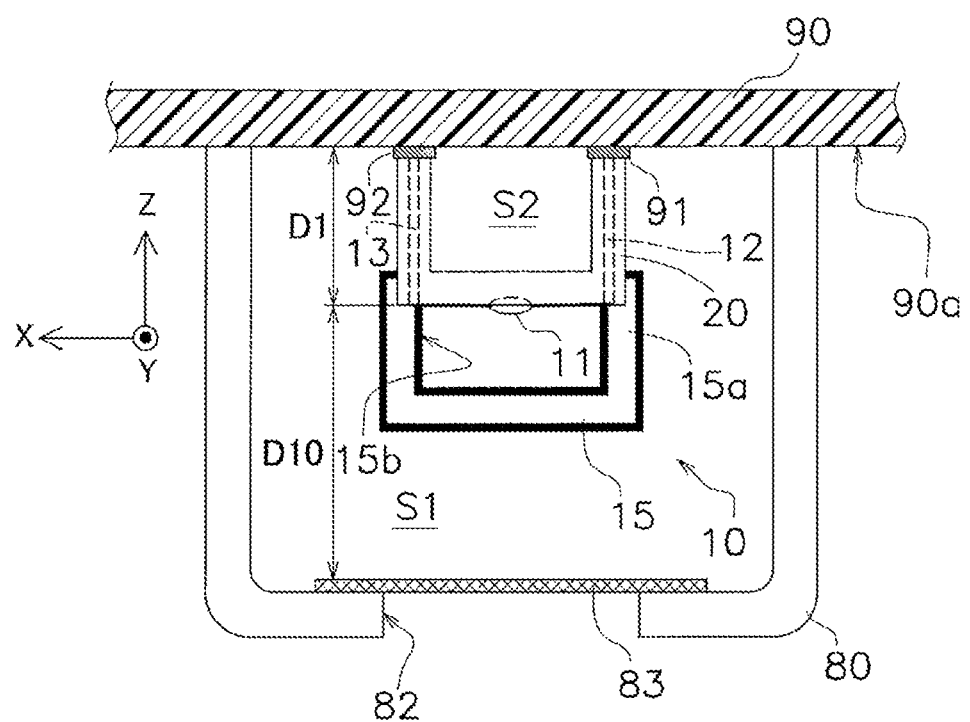
FIG. 2 is a schematic diagram illustrating an example of the configuration of a gas sensor mounted on a printed circuit board.

As illustrated in FIG. 2, the gas sensor 10 is disposed so as to project from, for example, a printed circuit board 90 serving as a wiring member. Because hydrogen is lighter than air, the gas sensor 10 projects downward from a bottom surface 90a of the printed circuit board 90. Although this embodiment describes a case where the gas sensor 10 is provided projecting downward from the printed circuit board 90, the direction in which the gas sensor 10 projects is not limited to this. A first wire 91 and a second wire 92 are provided on the printed circuit board 90. The connection point Pa illustrated in FIG. 1, to which the first electrode terminal 12 is connected, is located in the first wire 91. Likewise, the connection point Pc illustrated in FIG. 1, to which the second electrode terminal 13 is connected, is located in the second wire 92.

The gas sensor 10 is contained within a sensor cavity S1 surrounded by a sensor casing 80. An opening 82 that communicates with the sensor cavity S1 is formed in a lower part of the sensor casing 80. The opening 82 is completely covered by a water-repellent film 83. Accordingly, the hydrogen to be measured reaches the gas sensor 10 having permeated the water-repellent film 83. The opening 82 is covered by the water-repellent film 83 in order to prevent foreign objects, particularly, water droplets, from reaching the gas sensor 10.

The gas sensor 10 includes a cap 15 for protecting the resistor 11. The cap 15 has a frame shape, and an opening 15b through which hydrogen passes is formed in each of six faces of the cap 15. In other words, the cap 15 is constituted by a parallelepiped-shaped frame 15a having six open faces. This frame-shaped cap 15 can be manufactured by, for example, subjecting a plate-shaped member to a drawing process and then punching holes in the member. As used here, "frame-shaped" is a concept including a skeleton shape in which rod-shaped members are combined into a parallelepiped shape. Although a frame-shaped cap 15 is used here, the shape of the cap 15 is not limited to a frame shape. The resistor 11 is connected between the first electrode terminal 12 and the second electrode terminal 13. A housing 20 is a resin-molded member covering the first electrode terminal 12 and the second electrode terminal 13. For example, a thermoplastic resin can be used as the resin constituting the housing 20, and for example, nylon resin, polybutylene terephthalate resin (PBT resin), and liquid-crystal polymer resin can be given as examples of thermoplastic resins. Preferably, a water-repellent resin is used as the resin constituting the housing 20, to make it difficult for frost to form on the surface of the housing 20.

Figure 3:
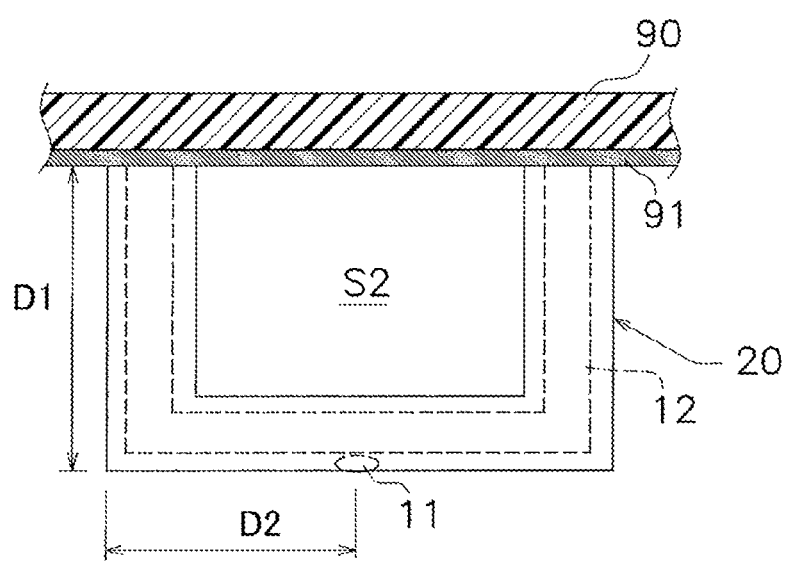
FIG. 3 is a schematic diagram illustrating a housing of a gas sensor, a first electrode terminal, and a second electrode terminal.

The resistor 11 of the gas sensor 10 is distanced from the printed circuit board 90 by a distance D1. A water vapor diffusion cavity S2 is formed spanning from the resistor 11 to the printed circuit board 90. Water vapor produced when hydrogen is combusted at the resistor 11 passes through the water vapor diffusion cavity S2 and reaches the bottom surface 90a of the printed circuit board 90. As such, the formation of frost starts primarily at the bottom surface 90a of the printed circuit board 90. While FIG. 2 illustrates the gas sensor 10 from the front, FIG. 3 schematically illustrates the gas sensor 10 as viewed from the side on which the first wire 91 is located. In FIG. 3, neither the sensor casing 80 nor the cap 15 are illustrated. As can be seen from FIGS. 2 and 3, for frost arising from water produced when hydrogen is combusted at the resistor 11 to reach the resistor 11, the frost is required to propagate downward from the printed circuit board 90 by the distance D1, and furthermore propagate horizontally by a distance D2. Otherwise, the frost will not reach the resistor 11. In this manner, problems caused by frost are suppressed by extending the distance over which the frost is required to propagate to D1+D2.

(2-1) First Electrode Terminal, Second Electrode Terminal, and Housing

Figure 6:
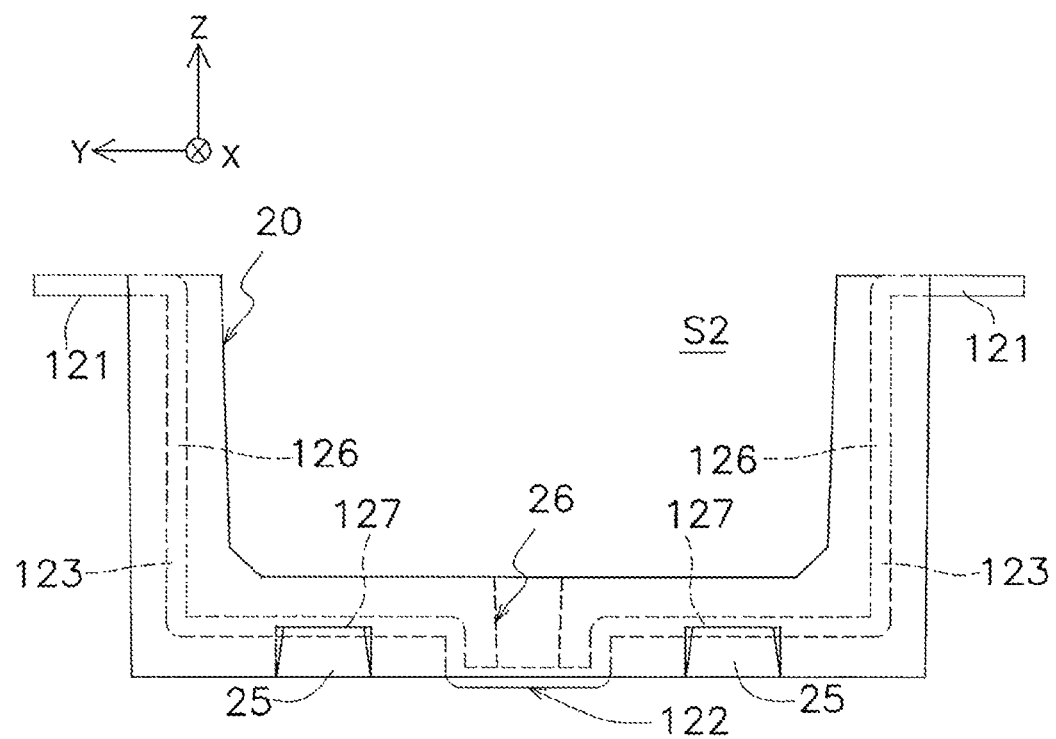
FIG. 6 is a side view illustrating an example of the configuration of a housing, a first electrode terminal, and a second electrode terminal.
Figure 7:
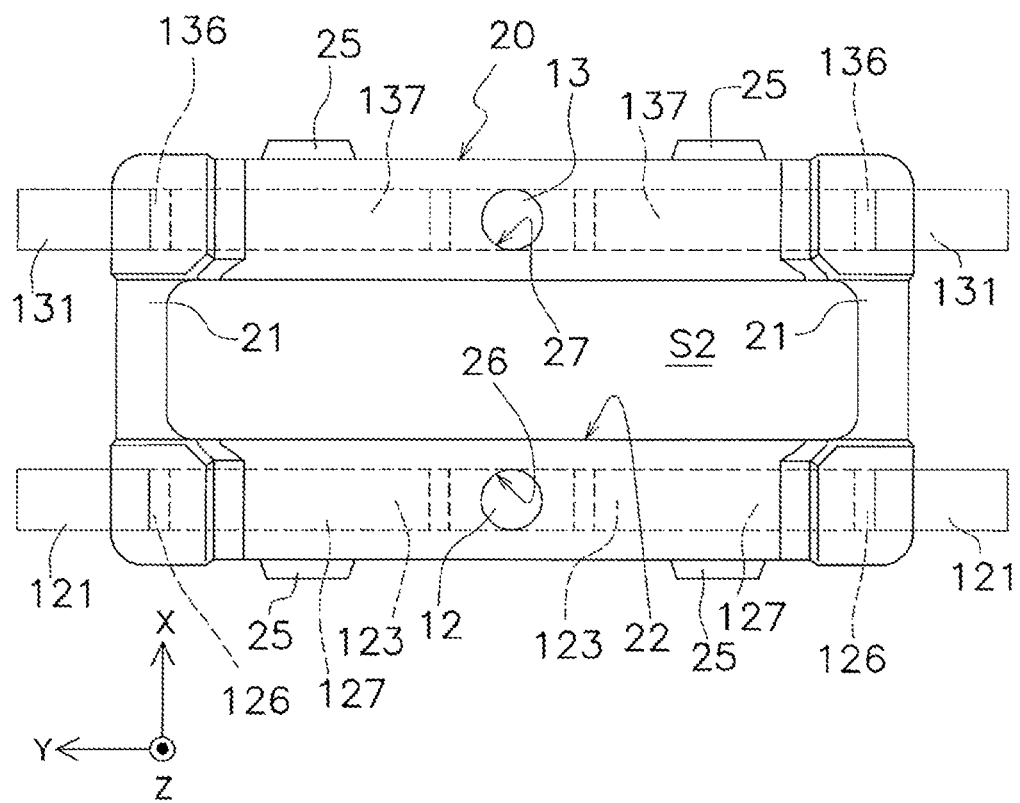
FIG. 7 is a plan view illustrating an example of the configuration of a housing, a first electrode terminal, and a second electrode terminal.

FIGS. 4 to 7 illustrate the configurations of the first electrode terminal 12, the second electrode terminal 13, and the housing 20. The first electrode terminal 12 and the second electrode terminal 13 are formed by bending a plate-shaped member made from a metal or alloy having good conductivity. For example, stainless steel or nickel silver, which is an alloy of copper, zinc, and nickel, can be used for the member constituting the first electrode terminal 12 and the second electrode terminal 13. The first electrode terminal 12 of the gas sensor 10, which is surface-mounted on the printed circuit board 90 serving as the wiring member, includes first connection parts 121 bent so as to be parallel to the first wire 91. A first base part 122, which is connected to one end of the resistor 11, is part of a first arm part 123, and is a part that projects vertically downward (in a Z axis direction) in the first arm part 123. The first base part 122 is a plane, parallel to an XY plane, exposed on the lower side. The first arm part 123 branches and extends from the first base part 122 in two directions, namely positive and negative Y axis directions. In other words, the first arm part 123 branches and extends in two directions from one end of the resistor 11 and connects to the two first connection parts 121. As illustrated in FIGS. 6 and 7, the first arm part 123 includes first vertical parts 126 extending in the Z axis direction (the vertical direction), and first horizontal parts 127 extending in the Y axis direction (the horizontal direction). The first vertical parts 126 and the first horizontal parts 127 are also coated with a thermoplastic resin.

The second electrode terminal 13 of the gas sensor 10, which is surface-mounted on the printed circuit board 90 serving as the wiring member, has second connection parts 131 bent so as to be parallel to the second wire 92. A second base part 132, which is connected to the other end of the resistor 11, is part of a second arm part 133, and is a part that projects vertically downward (in the Z axis direction) in the second arm part 133. The second base part 132 is a plane, parallel to an XY plane, exposed on the lower side. The second arm part 133 branches and extends from the second base part 132 in two directions, namely the positive and negative Y axis directions. In other words, the second arm part 133 branches and extends in two directions from the other end of the resistor 11 and connects to the two second connection parts 131. The second arm part 133 (illustrated in FIG. 4) includes second vertical parts 136 (illustrated in FIG. 7) extending in the Z axis direction (the vertical direction), and second horizontal parts 137 (illustrated in FIG. 7) extending in the Y axis direction (the horizontal direction). The second vertical parts 136 and the second horizontal parts 137 are also coated with a thermoplastic resin. The structure in which the above-described first vertical parts 126 and first horizontal parts 127, and the above-described second vertical parts 136 and second horizontal parts 137, are coated with a thermoplastic resin, can be formed through insert molding, for example. Note that openings 26 (illustrated in FIGS. 6 and 7) and 27 (illustrated in FIG. 7) are formed on the sides opposite from the first base part 122 (illustrated in FIG. 6) and the second base part 132 (illustrated in FIG. 4).

The above-described first horizontal parts 127 of the first arm part 123 correspond to a first separation part that extends in the horizontal direction from the one end of the resistor 11 and allows the first arm part to be separated from the resistor 11 in the horizontal direction. The second horizontal parts 137 of the second arm part 133 correspond to a second separation part that extends in the horizontal direction from the other end of the resistor 11 and allows the second arm part to be separated from the resistor 11 in the horizontal direction. The first horizontal parts 127 serving as the first separation part and the second horizontal parts 137 serving as the second separation part are also coated with a resin. Coating these parts with a resin makes it more difficult for frost to propagate than in a case where the metal first arm part 123 and second arm part 133 are exposed. Note that the effect of suppressing the propagation of frost will still be achieved even in a case where the first separation part and the second separation part are only partially coated with a resin instead of being completely coated.

The first electrode terminal 12 and the second electrode terminal 13 are bridged by bridge parts 21 of the housing 20 at positions located substantially as far from the printed circuit board 90 as the resistor 11. With the exception of the bridge parts 21, the first horizontal parts 127 of the first arm part 123 and the second horizontal parts 137 of the second arm part 133 are insulation-coated so as to be isolated from each other. As a result, an opening 22 is formed directly above the location where the resistor 11 is disposed, or in other words, between the resistor 11 and the printed circuit board 90. By forming the opening 22, the water vapor diffusion cavity S2, which continues uninterrupted to the printed circuit board 90, is formed above the resistor 11.

Additionally, the thermoplastic resin coating the first vertical parts 126 of the first arm part 123 is separated from the thermoplastic resin coating the second vertical parts 136 of the second arm part 133. In other words, the first arm part 123 is separated from the second arm part 133 and insulation-coated with the thermoplastic resin, from the vicinity of the first connection parts 121 to the vicinity of a position located at substantially the same height as the resistor 11. That is, the first arm part 123 and the second arm part 133 are isolated from each other and insulation-coated over a distance D3 illustrated in FIG. 4. An opening 23 opening on the side where the printed circuit board 90 is located is also formed as a result of the first arm part 123 and the second arm part 133 being separated and insulation-coated in this manner.

As illustrated in FIG. 6, the first arm part 123 is bent into an L shape in two locations. By being bent into an L shape in two locations, the first arm part 123 substantially has an overall C shape when viewed from the side. Like the first arm part 123, the second arm part 133 is bent into an L shape in two locations. By being bent into an L shape in two locations, the second arm part 133 substantially has an overall C shape when viewed from the side. Here, the first arm part 123 and the second arm part 133 branch in two directions, and therefore have overall C shapes, but a configuration in which the first arm part 123 and the second arm part 133 are not branched in two directions is also possible. For example, a configuration in which the first arm part 123 and the second arm part 133 are cut off in the centers of the first base part 122 and the second base part 132, i.e., in which the first base part 122 and the second base part 132 have L shapes when viewed from the side, is also possible. In this case, there are one each of the first connection parts 121 and the second connection parts 131, which does provide less stability than when there are two each of the first connection parts 121 and the second connection parts 131. However, such a configuration, in which the base parts have L shapes when viewed from the side, does not interfere with practical use.

The housing 20 is provided with claws 25 in four locations for attaching the cap 15. The claws 25 further project at the upper portion than at the lower portion. When the cap 15 is attached from below, the claws 25 catch and secure the cap 15.

(2-2) Resistor

Figure 8:
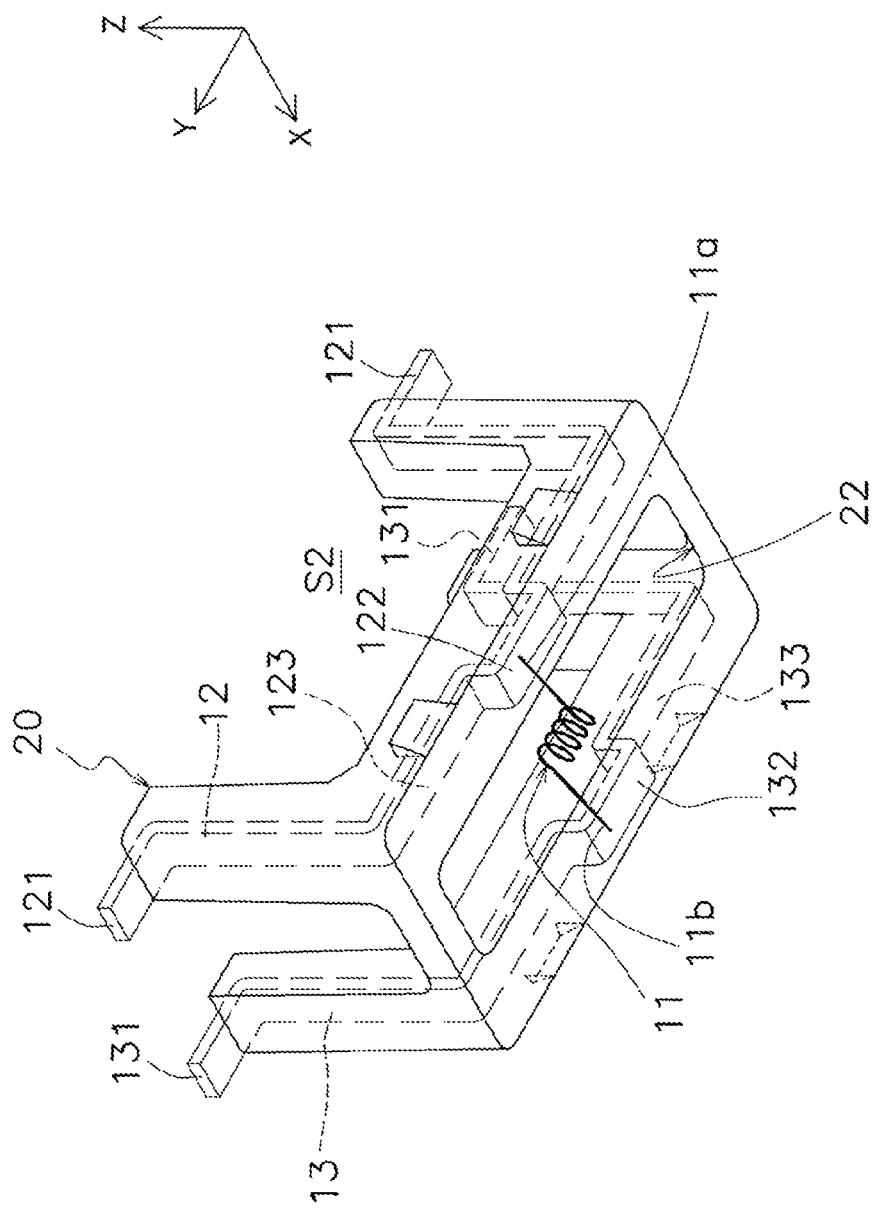
FIG. 8 is a perspective view illustrating an example of a state in which a resistor is attached to a housing.

FIG. 8 illustrates the housing 20 to which the resistor 11 is attached, from a lower diagonal direction. As illustrated in FIG. 8, one end 11a of the resistor 11 is connected to the first base part 122 of the first electrode terminal 12, and the other end 11b of the resistor 11 is connected to the second base part 132 of the second electrode terminal 13. The area vertically above the resistor 11 (in the Z axis direction) communicates with the water vapor diffusion cavity S2 through the opening 22.

The resistor 11 is formed by winding a platinum wire into a coil. The platinum wire is approximately several tens of μm in diameter, for example, and the coil is approximately several hundreds of μm in diameter, for example. The resistor 11 holds palladium, which serves as a catalyst, on the surface of the coil part.

(2-3) Cap

Figure 9:
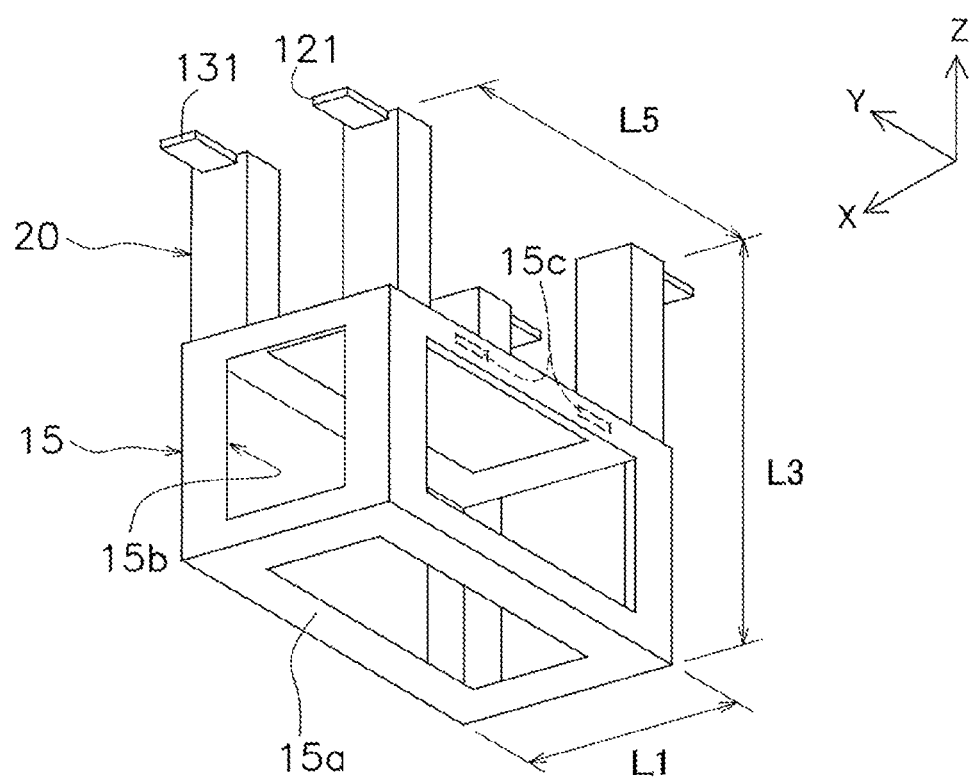
FIG. 9 is a perspective view schematically illustrating an example of a state in which a cap is attached to a housing.
Figure 10:
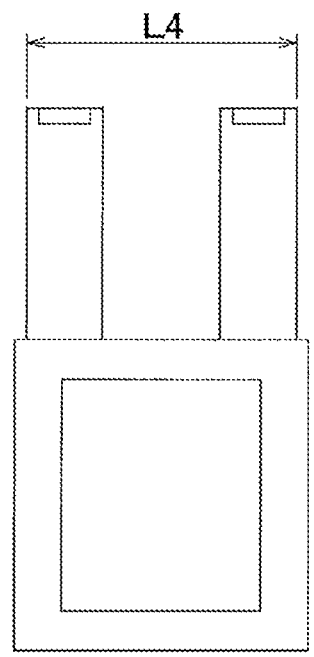
FIG. 10 is a front view schematically illustrating an example of a state in which a cap is attached to a housing.
Figure 11:
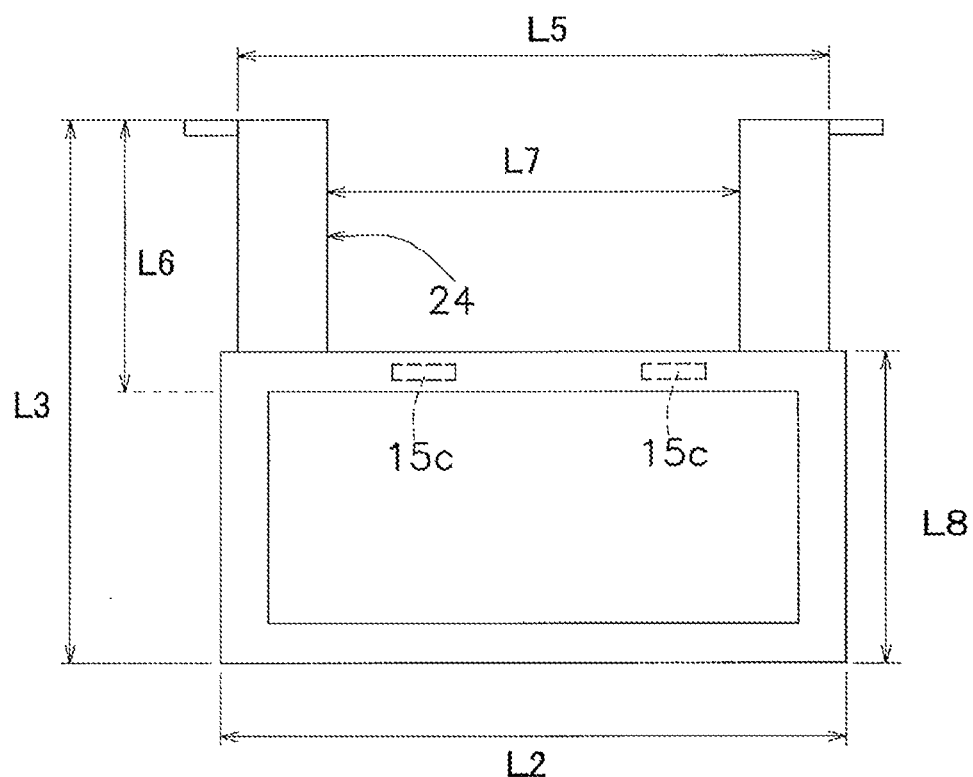
FIG. 11 is a side view schematically illustrating an example of a state in which a cap is attached to a housing.

FIGS. 9 to 11 schematically illustrate a state in which the cap 15 is attached to the housing 20. The cap 15 has a frame shape constituted by the frame 15a, which is formed from an iron-nickel alloy, for example. Using a three-dimensional shape that is only skeletal in this manner makes it easy for hydrogen to reach the resistor 11. The frame 15a is arranged at the positions of twelve sides of a parallelepiped. The frame 15a is constituted by angle bars (L angles), for example. The gaps between opposing parts of the frame 15a are set to widths into which a finger cannot fit through. There is thus no chance of a finger fitting through from the opening 15b and contacting the resistor 11 when the cap 15 is attached. The cap 15 can protect the resistor 11 from other foreign objects, aside from fingers, as well. Holes 15c are formed in the cap 15, on the side thereof that comes into contact with the housing 20. The claws 25 of the housing 20 engage with these holes 15c.

The following are reference values pertaining to the sizes of the housing 20 and the cap 15. When the housing 20 and the cap 15 are combined, a length L1 in the X direction is, for example, approximately from 3 to 4 mm, a length L2 in the Y direction is, for example, approximately from 6 to 9 mm, and a length L3 in the Z direction is, for example, approximately from 5 to 7 mm. Although a length L4 of the housing 20 in the X direction is obtained by subtracting the thickness of the frame 15a of the cap 15 from the length L1 of the cap 15 in the X direction, the frame 15a is thin and thus L4 is substantially equal to L1. Likewise, although a length L5 of the housing 20 in the Y direction is obtained by subtracting the thickness of the frame 15a from the length L2 of the cap 15 in the Y direction, the frame 15a is thin and thus L5 is substantially equal to L2. A length L6 of the housing 20 in the Z direction is approximately from 3 to 5 mm, for example. A length L7 of an opening 24 in the housing 20 is approximately from 4 to 7 mm, for example. A length L8 of the cap 15 in the Z direction is approximately from 2.5 to 5 mm, for example.

(3) Variations (3-1) Variation 1A

The foregoing first embodiment describes a case where the first electrode terminal 12 and the second electrode terminal 13 are bent into L shapes. However, the shapes of the first electrode terminal 12 and the second electrode terminal 13 are not limited to such shapes. For example, the terminals may have shapes that are semicircular when viewed from the side, as with the first electrode terminal 12 (or the second electrode terminal 13) illustrated in FIG. 12. This configuration makes it possible to increase a distance L11 from the printed circuit board 90 to the resistor 11 across the housing 20, while keeping a distance L10 from the resistor 11 to the printed circuit board 90 (a length in the Z axis direction) and a distance L9 from the resistor 11 to the end of the housing 20 (a length in the X axis direction) short.

(3-2) Variation 1B

The foregoing first embodiment describes a case where the housing 20 is attached to the printed circuit board 90 using four arms, by configuring the first electrode terminal 12 and the second electrode terminal 13 so as to branch and extend in two directions from the one end 11a and the other end 11b of the resistor 11. However, a configuration in which the housing 20 is attached to the printed circuit board 90 using two arms can also be implemented by configuring the first electrode terminal 12 and the second electrode terminal 13 to each extend in the positive or negative X axis direction from the one end 11a and the other end 11b of the resistor 11, as described earlier.

Additionally, the number of arms in the housing 20 is not limited to two or four, and may be three, or five or more.

(3-3) Variation 1C

In the foregoing first embodiment, the printed circuit board 90 is provided so as to cover the area above the water vapor diffusion cavity S2. However, a configuration is also possible in which an opening is provided in the printed circuit board 90 or the gas sensor 10 is provided at an end part of the printed circuit board 90 so that the water vapor diffusion cavity S2 extends through the printed circuit board 90 or the upper area of the water vapor diffusion cavity S2 is not covered by the printed circuit board 90.

(4) Other Embodiments (4-1)

Second Embodiment

Although the first embodiment of the present invention has been described above, the present invention is not limited to the foregoing embodiment, and many variations are possible without departing from the essential spirit of the invention. In particular, multiple embodiments and variations described in this specification can be combined optionally, as needed.

Figure 13:
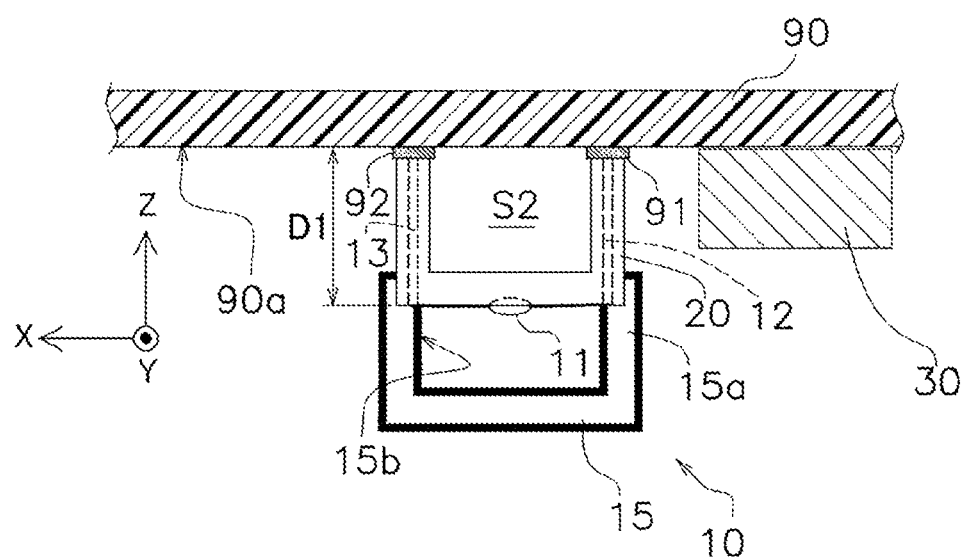
FIG. 13 is a schematic diagram illustrating the configuration of a gas sensor according to a second embodiment.

The foregoing first embodiment describes a case where mounted components that produce heat by themselves are not taken into consideration. However, as illustrated in FIG. 13, a mounted component 30 that produces heat by itself may be disposed nearby the gas sensor 10 and combined with the gas sensor 10. In this case, it is preferable that the mounted component that produces heat by itself be a mounted component that operates along with the operation of an electric circuit into which the gas sensor 10 is incorporated. A chip resistor of the electric circuit into which the gas sensor 10 is incorporated can be given as an example of such a mounted component. For example, in a case where the first fixed resistor 3 and the second fixed resistor 4 illustrated in FIG. 1 are configured as chip resistors, those chip resistors are disposed nearby the gas sensor 10 as mounted components 30. In a case where the mounted components 30 that produce heat by themselves are used to heat the bottom surface 90a of the printed circuit board 90 directly above the resistor 11 over substantially the same amount of time and eliminate the influence of frost, the distance D1 between the resistor 11 of the gas sensor 10 and the printed circuit board 90 can be reduced even further.

(4-2)

Third Embodiment

The foregoing second embodiment describes a case where the bottom surface 90a of the printed circuit board 90 directly above the resistor 11 is heated using the mounted component 30, which produces heat by itself. However, the mounted component 30 may instead be a dedicated heater. It is sufficient that the dedicated heater prevent frost from being formed in particular. As such, the heater need not heat to the boiling point of water or above. For example, the heater is configured to turn off at a switching temperature of from 1° C. to 50° C., and more preferably, from 5° C. to 10° C. For example, the heater can be configured to turn off when the temperature reaches 5° C. by using a temperature sensor and a switching element. In a case where the gas sensor 10 is installed in an automobile, the power for driving the gas sensor 10 and the heater is taken from the battery of the automobile, and it is therefore necessary to drive the gas sensor 10 and the heater with as little power as possible.

(5) Features (5-1)

As described above, the gas sensor 10 is disposed projecting from the printed circuit board 90 (an example of a wiring member) serving as a mounting target and including the first wire 91 and the second wire 92. Although the printed circuit board 90 is described as an example of the wiring member here, the wiring member is not limited to a printed circuit board. The wiring member may be any location of a member where the first wire 91 and the second wire 92 can be provided, such as a wiring region in an electrical component box or a plastic case.

As described earlier, the gas sensor is not limited to a gas sensor that detects hydrogen. The detection target may be any gas that produces water ($H_2O$) when combusted. However, a gas sensor that detects a gas lighter than air, such as hydrogen, is provided projecting downward from the wiring member because the gas to be detected rises from the bottom.

The first electrode terminal 12 includes at least one first connection part 121 connected to the first wire 91, and the first arm part 123 extending from the first connection part 121 to the one end 11a of the resistor 11. Likewise, the second electrode terminal 13 includes at least one second connection part 131 connected to the second wire 92, and the second arm part 133 extending from the second connection part 131 to the other end 11b of the resistor 11. Although the foregoing first embodiment describes a case where there are two each of the first connection part 121 and the second connection part 131, the configuration may be such that one each of the first connection part 121 and the second connection part 131 are provided in a case where there are two arms of the housing 20, as described in variation 1B.

The first electrode terminal 12 and the second electrode terminal 13 are fixed to each other, with at least part of the first arm part 123 and at least part of the second arm part 133 coated with insulation, to form the water vapor diffusion cavity S2 extending from the resistor 11 to the printed circuit board 90. In the first embodiment, the arm parts are completely coated with a thermoplastic resin, aside from the first base part 122 and the second base part 132 for attaching the resistor 11, and the parts on the opposite side of the base parts facing the openings 26 and 27. In the first embodiment, the water vapor diffusion cavity S2 extends to the bottom surface 90a of the printed circuit board 90, but a thin protective film, from approximately several µm to several hundreds of µm, which makes contact with the bottom surface 90a and covers the bottom surface 90a, may be provided so that water vapor does not come into direct contact with the printed circuit board 90. When such a protective film is provided, the water vapor diffusion cavity S2 does not reach the printed circuit board 90 (the wiring member), but does reach the vicinity thereof, and thus the same effects can be achieved as when the water vapor diffusion cavity S2 reaches the printed circuit board 90, which will be described later.

According to the gas sensor configured in this manner, the water vapor diffusion cavity S2, which extends from the resistor 11 to the printed circuit board 90 or the vicinity thereof, is formed between the resistor 11 and the printed circuit board 90. Accordingly, water vapor produced when hydrogen is combusted reaches the printed circuit board 90 or the vicinity thereof through the water vapor diffusion cavity S2, and thus frost starts forming primarily on the printed circuit board 90 or in the vicinity thereof (e.g., the above-described protective film). As a result, the combustion time necessary for frost to form can be increased, without consuming heating energy for melting the frost, while effectively using the entire lengths of the first arm part 123 and the second arm part 133. This makes it possible to maintain a state where gas can be detected without being affected by frost for a long period of time.

Figure 14:
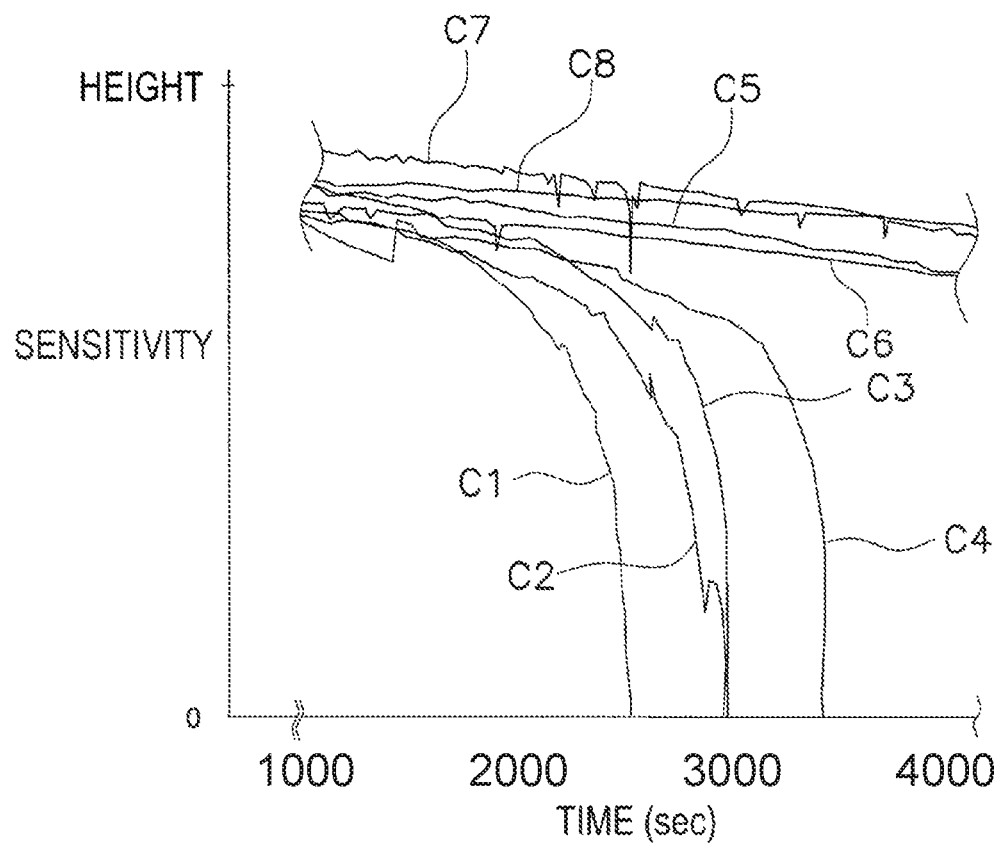
FIG. 14 is a graph showing a relationship between sensitivity and time when the position and the like of a resistor of a gas sensor is varied.

FIG. 14 illustrates a relationship between the output of the gas sensor 10 and time, using the distance D from the printed circuit board 90 to the resistor 11 and a distance D10 from the resistor 11 to the opening 82 in the sensor casing 80 as parameters. In FIG. 14, curves C1 and C2 indicate the output when the distance D1 is 1 mm and the distance D10 is 3 mm; a curve C3 indicates the output when the distance D1 is 1 mm and the distance D10 is 6 mm; a curve C4 indicates the output when the distance D1 is 1 mm and the distance D10 is 9.9 mm; a curve C5 indicates the output when the distance D1 is 2 mm and the distance D10 is 6 mm; a curve C6 indicates the output when the distance D1 is 2 mm and the distance D10 is 9.9 mm; a curve C7 indicates the output when the distance D1 is 3 mm and the distance D10 is 6 mm; and a curve C8 indicates the output when the distance D1 is 3 mm and the distance D10 is 9.9 mm. However, the measurements of the curves C1 to C8 indicated in FIG. 14 were taken under conditions where the ambient temperature was minus 35° C., and the distance D2 from the parts of the first electrode terminal 12 and the second electrode terminal 13 bent into L shapes to the resistor 11 was 2.5 mm. From these results, it can be seen that increasing the distance D1 suppresses a drop in sensitivity. To take a different perspective, it can furthermore be seen that increasing the distance D1+D2 suppresses a drop in sensitivity.

(5-2)

The first electrode terminal 12 and the second electrode terminal 13 are fixed to each other by being bridged by the bridge parts 21 at positions distanced from the printed circuit board 90 by the distance D1, which is substantially the same distance as the resistor 11. According to this configuration, the bridge parts 21 bridging the first electrode terminal 12 and the second electrode terminal 13 are not present between the printed circuit board 90 and the resistor 11. As a result, most of the water vapor produced at the resistor 11 rises upward, which makes it difficult for the water vapor to reach the bridge parts 21 located at the same height as the resistor 11. It is thus difficult for frost to start forming from the bridge parts 21, increasing the distance over which the frost propagates.

Figure 15:
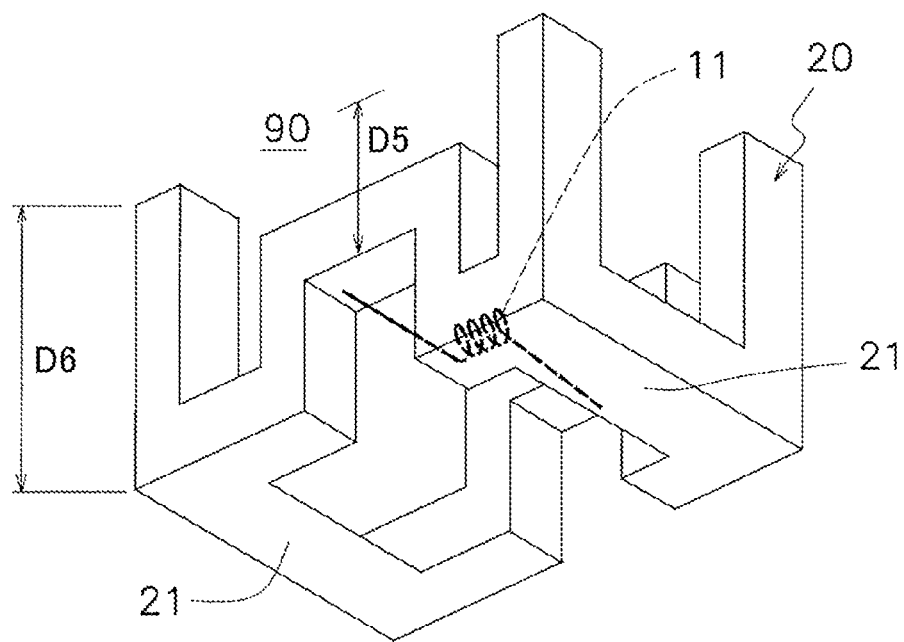
FIG. 15 is a perspective view illustrating another example of the configuration of a housing, a first electrode terminal, and a second electrode terminal.

For example, as illustrated in FIG. 15, in a case where a distance D6 from the bridge parts 21 to the printed circuit board 90 is greater than a distance D5 from the printed circuit board 90 to the resistor 11, the water vapor produced at the resistor 11 rising upward means that frost will not start forming on the bridge parts 21, which are lower than the resistor 11. This makes it possible to increase the distance over which the frost propagates.

(5-3)

Figure 4:
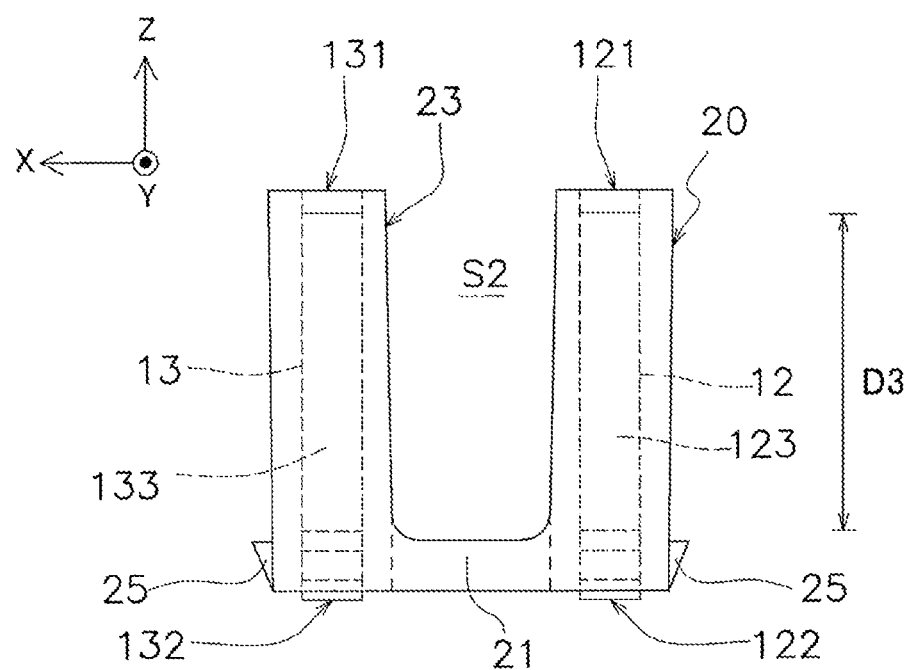
FIG. 4 is a front view illustrating an example of the configuration of a housing, a first electrode terminal, and a second electrode terminal.
Figure 5:
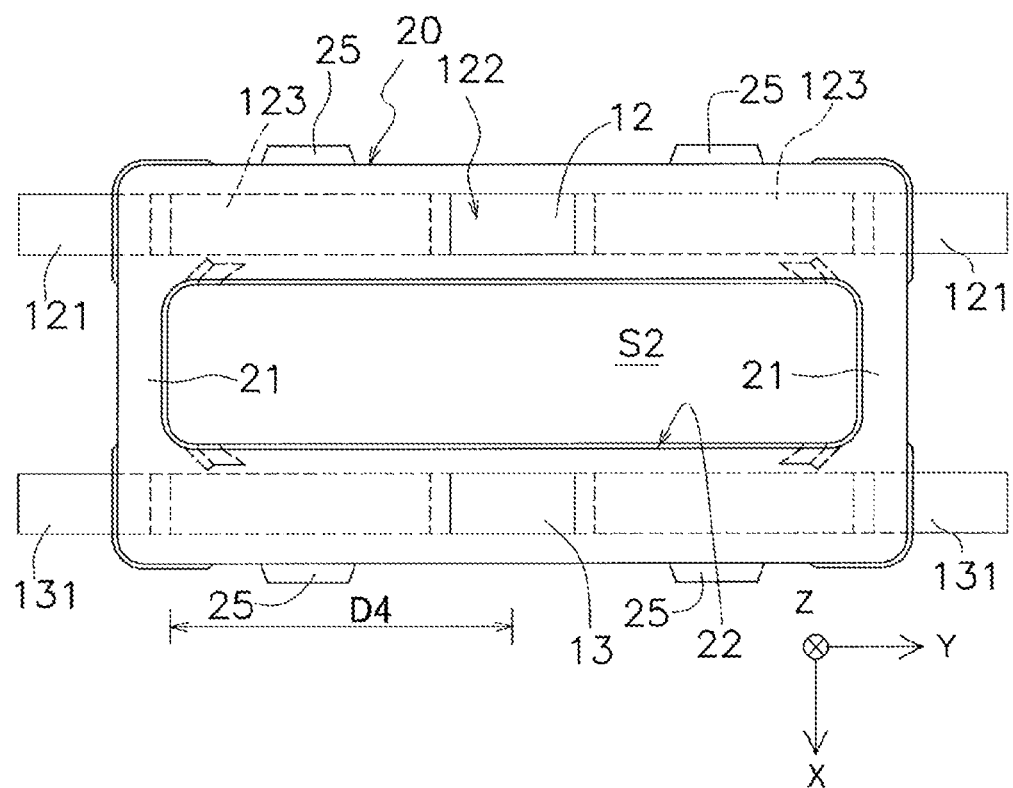
FIG. 5 is a bottom view illustrating an example of the configuration of a housing, a first electrode terminal, and a second electrode terminal.

Additionally, the first arm part 123 and the second arm part 133 are configured so that horizontal direction lengths of the arm parts expressed by X coordinates and Y coordinates in a plane perpendicular to a Z axis (a distance D4 indicated in FIG. 5) are substantially the same as vertical direction lengths of the arm parts expressed by Z coordinates and extending in the vertical direction from the printed circuit board 90 (the distance D3 indicated in FIG. 4). According to this configuration, the vertical direction size from the printed circuit board 90 and horizontal direction size are suppressed, while at the same time making the distance over which frost propagates approximately twice as long compared to a case where the first arm part 123 and the second arm part 133 are erected straight in the vertical direction. As a result, it takes approximately twice as long for the frost to form and reach the resistor 11, which in turn makes it possible to approximately double the time for which the sensitivity can be maintained during continuous use. In actual use cases, the frost sometimes melts during use, and there are thus situations where the time for which sensitivity can be maintained is extended without extending the lengths of the first arm part 123 and the second arm part 133.

(5-4)

Additionally, in the gas sensor 10 according to the foregoing first embodiment, both the first arm part 123 and the second arm part 133 are bent into L shapes. Accordingly, using a simple structure, the distance along the first arm part 123 and the second arm part 133 over which frost propagates from the printed circuit board 90 to the resistor 11 can be increased while at the same time suppressing the vertical direction heights of the first electrode terminal 12 and the second electrode terminal 13. Note that the number of L-shaped bends is not limited to 1, and the same effects can be achieved even with multiple L-shaped bends.

(5-5)

In the gas sensor 10 according to foregoing first embodiment, as illustrated in FIG. 8, the first arm part 123 branches and extends in two directions from the one end 11a of the resistor 11, and includes two of the first connection parts 121 connected to the first wire 91; and the second arm part 133 branches and extends in two directions from the other end 11b of the resistor 11, and includes two of the second connection parts 131 connected to the second wire 92. According to this configuration, the branching first arm part 123 and the branching second arm part 133 provide a total of four arms supporting the gas sensor 10, which improves the stability with which the gas sensor 10 is installed on the printed circuit board 90. In this case, soldering the first connection parts 121 and the second connection parts 131 to the first wire 91 and the second wire 92, respectively, for all four of the arms increases the installation strength as well.

(5-6)

In the gas sensor 10 according to the foregoing first embodiment, the first arm part 123 and the second arm part 133 are separated from each other and insulation-coated with a resin, from the vicinity of the first connection parts 121 and the second connection parts 131 to the vicinity of a position located at substantially the same height as the resistor 11. In other words, the parts are separated and insulated from each other over the area indicated as the distance D3 in FIG. 4. According to this configuration, the parts of the surfaces of the first electrode terminal 12 and the second electrode terminal 13 that are coated by resin, which makes it difficult for frost to propagate, can be lengthened. This makes it possible to improve the effect of suppressing problems caused by frost.

(5-7)

In the gas sensor 10 according to the foregoing first embodiment, the first arm part 123 includes a first separation part that extends in the horizontal direction from the one end 11a of the resistor 11 and allows the first arm part 123 to be separated from the resistor 11 in the horizontal direction, and the first separation part is coated with a resin. The first separation part is, for example, the area from the one end 11a of the resistor 11 to a position distanced by the distance D4 in FIG. 5. Likewise, the second arm part 133 includes a second separation part that extends in the horizontal direction from the other end 11b of the resistor 11 and allows the second arm part 133 to be separated from the resistor 11 in the horizontal direction, and the second separation part is coated with a resin. The second separation part is, for example, the area from the other end 11b of the resistor 11 to a position distanced by the distance D4 in FIG. 5. Coating the first separation part and the second separation part with resin in this manner makes it more difficult for frost to form than in a case where the first electrode terminal 12 and the second electrode terminal 13 are exposed, and thus situations where frost reaches the resistor 11 can be suppressed.

Figure 16:
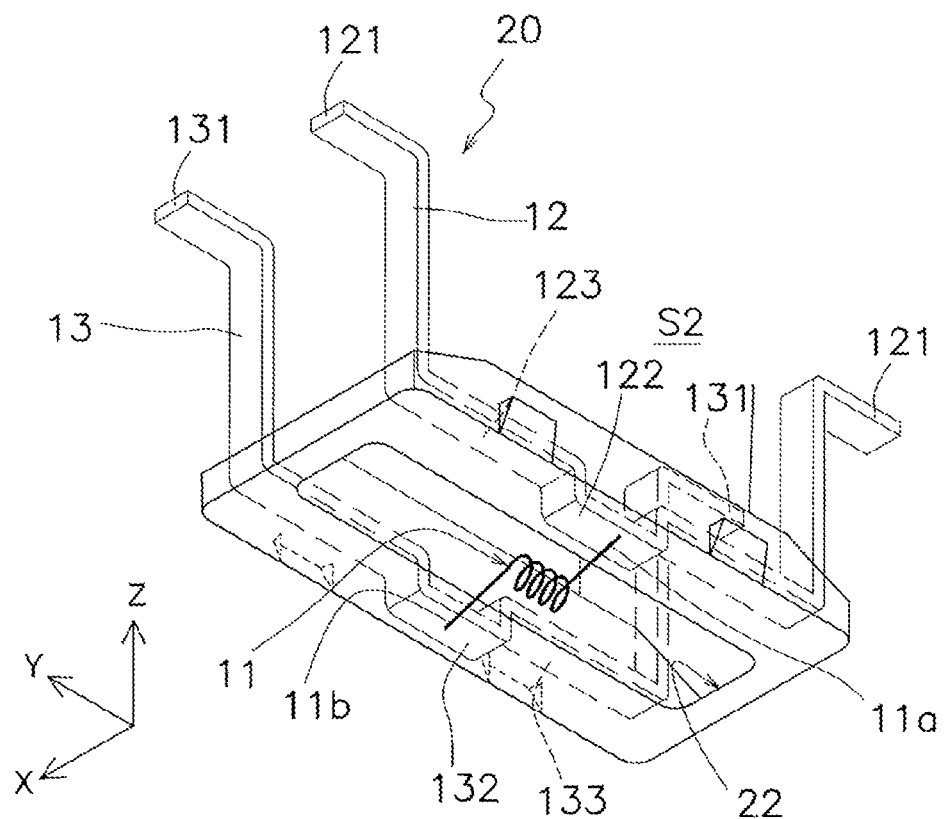
FIG. 16 is a perspective view illustrating another example of a state in which a resistor is attached to a housing.

A configuration is also possible in which the resin insulation coating is not applied to the parts of the first arm part 123 and the second arm part 133 extending straight in the Z axis direction from the first connection parts 121 and the second connection parts 131, as illustrated in FIG. 16.

Figure 12:
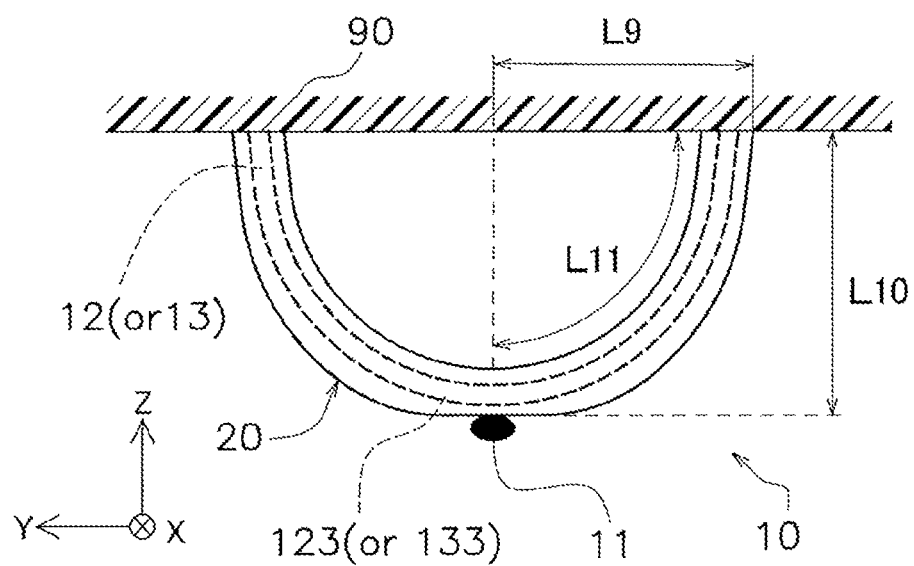
FIG. 12 is a side view schematically illustrating an example of another form for a housing.
Figure 17:
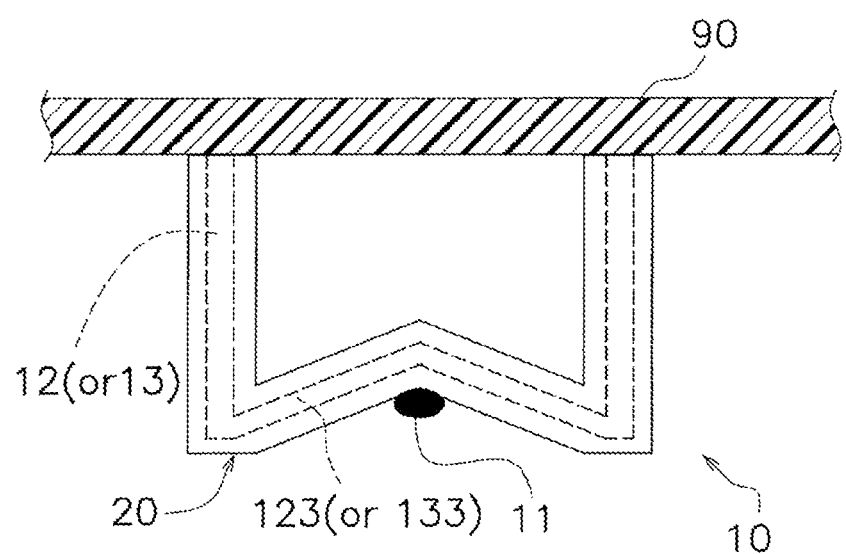
FIG. 17 is a side view schematically illustrating another example of another form for a housing.

Alternatively, a configuration may be employed in which the first arm part 123 and the second arm part 133 are formed extending not only in the horizontal direction but also in an oblique direction, in order to provide the first separation part and the second separation part for separating from the resistor 11 in the horizontal direction, as illustrated in FIGS. 17 and 12.

(5-8)

In the gas sensor 10 according to the foregoing first embodiment, the cap 15 covering the resistor 11 has a frame shape, as described with reference to FIGS. 9 to 11. Providing this cap 15 makes it possible to prevent hands and other foreign objects from contacting the resistor 11 when handling the gas sensor 10, and protect the resistor when handling the gas sensor, while at the same time ensuring that the cap 15 is not an obstruction when conducting the gas to be detected to the vicinity of the resistor 11. Accordingly, situations where the hydrogen sensitivity drops and defective devices are produced can be suppressed.

REFERENCE SIGNS LIST

1 Gas detection device
10 Gas sensor
11 Resistor
12 First electrode terminal
13 Second electrode terminal
15 Cap 20 Housing
21 Bridge part
90 Printed circuit board (an example of a wiring member)
91 First wire
92 Second wire
121 First connection part
123 First arm part
131 Second connection part
133 Second arm part
S1 Sensor cavity
S2 Water vapor diffusion cavity

The invention claimed is:

1. A gas sensor, disposed projecting from a wiring member serving as a mounting target and including a first wire and a second wire, the gas sensor being configured to detect a gas that produces water in a case that the gas is combusted by being supplied with a voltage from the first wire and the second wire and measuring a resistance value using the first wire and the second wire, the gas sensor comprising:
   a resistor holding a catalyst that facilitates combustion of the gas;
   a first electrode terminal connected between one end of the resistor and the first wire; and
   a second electrode terminal connected between another end of the resistor and the second wire,
   wherein the first electrode terminal includes at least one first connection part connected to the first wire, and a first arm part extending from the at least one first connection part to the one end of the resistor;
   the second electrode terminal includes at least one second connection part connected to the second wire, and a second arm part extending from the at least one second connection part to the other end of the resistor; and
   the first electrode terminal and the second electrode terminal are fixed to each other and form a water vapor diffusion cavity extending from the resistor to the wiring member or adjacent to the wiring member, the first arm part and the second arm part comprising vertical direction lengths extending in a vertical direction along a Z-axis from the wiring member and horizontal direction lengths in a plane along a X-axis and a Y-axis perpendicular to the Z-axis, at least part of the first arm part and at least part of the second arm part being coated with insulation using a housing.

2. The gas sensor according to claim 1,
wherein the housing comprises a bridge fixing the first electrode terminal and the second electrode terminal with each other by bridging the first electrode terminal and the second electrode terminal with each other, the bridge being located at substantially the same position as the resistor or a position further from the wiring member than a position of the resistor.

3. The gas sensor according to claim 1,
wherein the first arm part and the second arm part are configured such that the horizontal direction lengths of the first arm part and the second arm part are substantially the same as the vertical direction lengths.

4. The gas sensor according to claim 1,
wherein both the first arm part and the second arm part are bent into L shapes.

5. The gas sensor according to claim 1,
wherein the at least one first connection part includes first connection parts and the at least one second connection part includes second connection parts;
the first arm part branches and extends in two directions from the one end of the resistor, and includes two first connection parts of the first connection parts connected to the first wire; and
the second arm part branches and extends in two directions from the other end of the resistor, and includes two second connection parts of the second connection parts connected to the second wire.

6. The gas sensor according to claim 1,
wherein the first arm part and the second arm part are separated from each other and insulation-coated, from adjacent to the at least one first connection part and the at least one second connection part to adjacent to a position located at substantially the same height as the resistor.

7. The gas sensor according to claim 1,
wherein the first arm part includes a first separation part that extends in a horizontal direction or an oblique direction from the one end of the resistor and allows the first arm part to be separated from the resistor in the horizontal direction, the first separation part being coated with a resin; and
the second arm part includes a second separation part that extends in a horizontal direction or an oblique direction from the other end of the resistor and allows the second arm part to be separated from the resistor in the horizontal direction, the second separation part being coated with a resin.

8. The gas sensor according to claim 1, further comprising:
   a cap having a frame shape and configured to cover the resistor.

* * * * *